(12) United States Patent
Secq

(10) Patent No.: US 7,694,581 B2
(45) Date of Patent: Apr. 13, 2010

(54) COLLAR FOR MEASURING THE LATERAL DEFORMATION OF A TEST PIECE DURING COMPRESSION TESTS, SUCH AS UNIAXIAL OR TRIAXIAL COMPRESSION TESTS

(75) Inventor: Jean Secq, Villeneuve d'Asq (FR)

(73) Assignee: Universite des Sciences et Technologies de Lille, Villeneuve d'Asq (FR)

( * ) Notice: Subject to any disclaimer, the term of this patent is extended or adjusted under 35 U.S.C. 154(b) by 162 days.

(21) Appl. No.: 11/914,225

(22) PCT Filed: May 22, 2006

(86) PCT No.: PCT/FR2006/001164

§ 371 (c)(1),
(2), (4) Date: Nov. 12, 2007

(87) PCT Pub. No.: WO2006/125903

PCT Pub. Date: Nov. 30, 2006

(65) Prior Publication Data

US 2008/0184580 A1      Aug. 7, 2008

(30) Foreign Application Priority Data

May 24, 2005   (FR) .................................. 05 05204

(51) Int. Cl.
*G01N 3/08* (2006.01)
(52) U.S. Cl. .......................................... 73/818; 73/760

(58) Field of Classification Search ............ 73/760–818
See application file for complete search history.

(56) References Cited

U.S. PATENT DOCUMENTS

| 3,779,085 | A |   | 12/1973 | Rice |
|---|---|---|---|---|
| 3,791,205 | A | * | 2/1974 | Hooker .......................... 73/767 |
| 4,047,425 | A |   | 9/1977 | Handy et al. |
| 4,656,767 | A | * | 4/1987 | Tarrant .......................... 40/316 |
| 4,905,521 | A |   | 3/1990 | Wagner et al. |
| 5,483,836 | A |   | 1/1996 | Kinnebrew |
| 5,837,889 | A | * | 11/1998 | Slenker .......................... 73/81 |
| 7,520,177 | B2 | * | 4/2009 | Secq ............................. 73/795 |

FOREIGN PATENT DOCUMENTS

| FR | 2566531 | 12/1985 |
|---|---|---|
| FR | 2663121 | 12/1991 |
| FR | 2722565 | 1/1996 |

* cited by examiner

*Primary Examiner*—Max Noori
(74) *Attorney, Agent, or Firm*—Egbert Law Offices PLLC

(57) ABSTRACT

The invention relates to a collar for measuring the lateral deformation of a test piece during uniaxial or triaxial compression tests. According to the invention, the collar includes a metal hoop or a hoop that is made from composite materials, which can clasp the test piece and which is open. The free ends thereof are separated by a distance Δ. The inventive collar also includes a mechanism for directly or indirectly measuring the distance Δ. Between the free ends of the hoop, the mechanism includes at least one strain gauge.

8 Claims, 2 Drawing Sheets

COLLAR FOR MEASURING THE LATERAL DEFORMATION OF A TEST PIECE DURING COMPRESSION TESTS, SUCH AS UNIAXIAL OR TRIAXIAL COMPRESSION TESTS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The invention concerns a collar for measuring the lateral deformation of a test piece during compression tests, in particular uniaxial or triaxial.

It will find a particular application in a polyvalent triaxial test cell for sample geomaterials of rock, of soil, of cimentitious materials or of fabricated materials, on the sampling sites, in laboratory test conditions. Such samples, also called test pieces, cylindrical in shape, may be subjected to different pressure, load, temperature, and drainage conditions, wherein said parameters may be controlled using pressure, temperature, internal or external displacement sensors. The pressure stresses may be directed axially and/or to the lateral face of the sample.

2. Description of Related Art Including Information Disclosed Under 37 CFR 1.97 and 37 CFR 1.98.

Document FR-2.566.531 divulges a lateral displacement sensor, in the form of a collar, formed of a plurality of parallel rolls, hinged together, and capable of clamping the sample held by a spring-loaded system. Such collar enables to measure the lateral deformation of the sample while measuring the spacing of both last rolls.

Document FR-2.663.121 divulges a polyvalent triaxial test cell for geomaterials. Such cell includes a pressure chamber inside which is placed the cylindrical test piece. It includes at least one compression jack capable of exerting uniaxial thrust longitudinally to the test piece. A lateral pressure, and more particularly radial, is exerted on the test piece while subjecting the lateral face of said cylindrical test piece to the pressure of a fluid. A hydraulic compensation system enables moreover to balance the longitudinal and radial loads.

Also, the sample is immersed in a fluid, such as oil, and is protected from said fluid by means of a sheath in the form of a sleeve formed of an elastic diaphragm. In order to measure the lateral deformation of the sample, a collar of known type, formed of rolls, is placed around the sheath while hugging it.

Nevertheless, such a collar proves little satisfactory, since these rolls have a tendency to impress in the elastic wall of the diaphragm, thereby disturbing their displacement by rolling around the periphery of the sleeve.

Moreover, it has been noticed that the elasticity of the wall of the diaphragm twists the measurement, wherein the collar measures the lateral deformation of the sample, but also the lateral deformation of said diaphragm.

Moreover, the collar known aforementioned, formed of rolls, proves relatively cumbersome and requires a test cell whereof the pressure chamber is sufficiently large, in particular in width, to be installable.

BRIEF SUMMARY OF THE INVENTION

The aim of the present invention is to provide a collar measuring the lateral deformation of a test piece which remedies the shortcomings aforementioned, thereby enabling to increase the accuracy of the measurements.

Another aim of the invention is to provide a measuring collar, simple in its design and at low cost.

Another aim of the invention is to offer a protective sheath for specific test piece, suited to be used with a collar according to the invention.

Other aims and advantages of the present invention will appear from the following description, given solely by way of example and without being limited thereto.

The invention relates first of all to a collar for measuring the lateral deformation of a test piece during compression tests, in particular uniaxial or triaxial. The collar is formed of a metal ring or a ring made of composite materials, capable of clamping said test piece and being open. The free ends are spaced apart by a distance A, said collar exhibiting moreover means for measuring, directly or indirectly, the spacing 4 of said free ends of the ring, formed by at least one stress gauge.

The invention also relates to a sheath, intended for being used in a test cell, in order to protect a test piece, in particular mineral, rock and/or soil, or concrete. The sheath is formed by an elastic sleeve and is capable of cooperating with a measuring collar in particular according to the invention.

According to the invention, the sleeve exhibits, in its wall, at least two hard spots spread regularly on the circumference of said sleeve, being capable of forming resting points for said collar.

BRIEF DESCRIPTION OF THE SEVERAL VIEWS OF THE DRAWINGS

The invention will be understood better when reading the following description accompanied by the appended drawings.

DETAILED DESCRIPTION OF THE INVENTION

Figure 1:
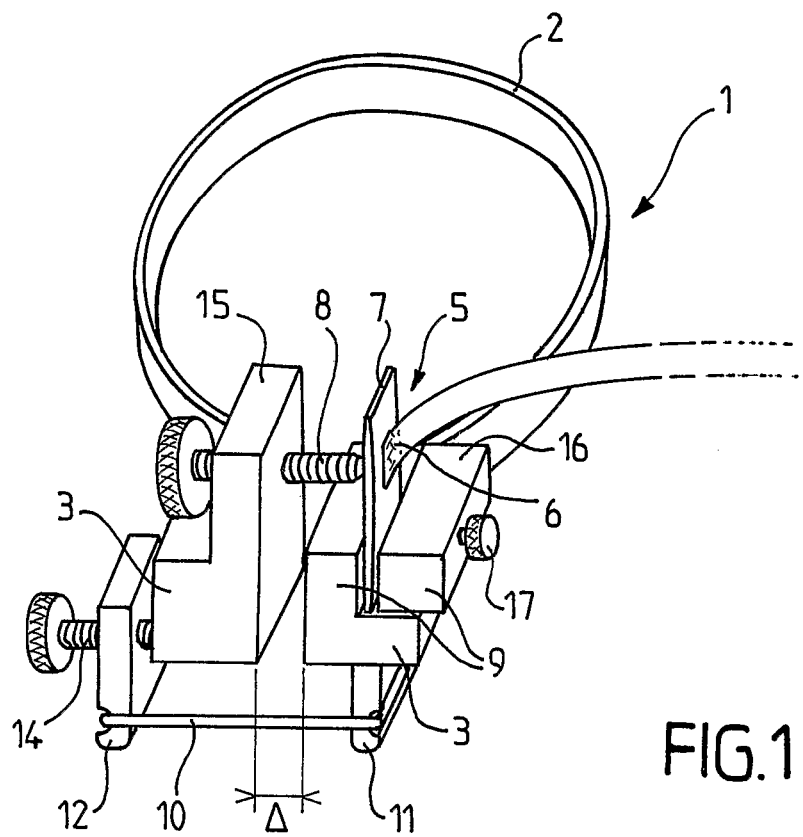
FIG. 1 is a perspective view of a measuring collar according to the invention.

The invention relates first of all to a collar for measuring the lateral deformation of a test piece during compression tests, in particular uniaxial or triaxial.

By lateral deformation is meant a deformation of the test piece in a plane perpendicular to the longitudinal axis of the cylindrical test piece.

According to the invention, the collar 1 is formed of a metal ring or a ring made of composite materials, capable of clamping said test piece. The ring 2 is open. The free ends 3 of the ring are spaced apart by a distance A. Said collar 1 exhibits moreover means 5 for measuring; directly or indirectly, the spacing A of said free ends 3 of the ring 2, the means being formed by at least one stress gauge 6.

The stress gauge, also called extensometric gauge, is an apparatus enabling to follow the deformation of materials subjected to stresses, by means of resistance variations of an electric conductor.

The metal ring, being made of composite materials, can be composed of a single-piece or two adjoining portions, for instance joined by welding, in particular rigid or semi-rigid. It enables the test piece to be clamped by hugging.

In an embodiment, the means 5 for measuring the spacing of said free ends of the ring are formed by four stress gauges.

Figure 2:
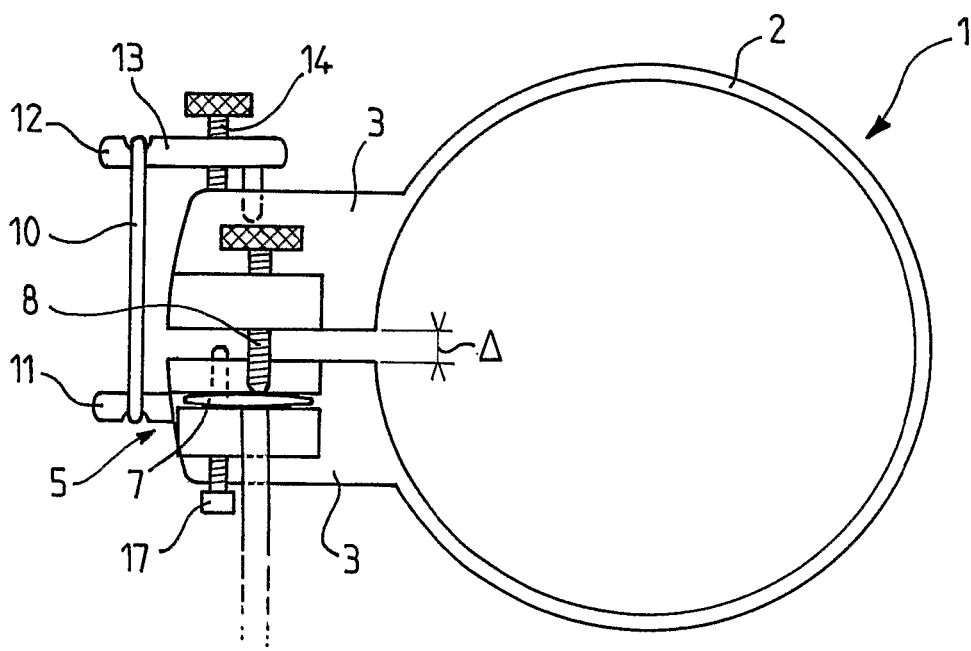
FIG. 2 is a diagrammatical top plan view of the measuring collar as illustrated on FIG. 1.

In a particular embodiment, illustrated on FIG. 1 or 2, the measuring means 5 are formed, on the one hand, by a resilient blade 7 fitted with said at least one stress gauge 6. The resilient blade 7 is pre-stressed and slaved to one of the free ends 3 of the ring 2. On the other hand, with a contact finger 8, the resilient blade 7 is slaved to the other end of the ring, being capable of causing the flection of the resilient blade during the deformation of the collar.

The free ends of the ring 3 are each spaced apart by a material protrusion, substantially parallel to one another.

As illustrated on FIG. 1 or 2, said resilient blade 7 is arranged at an end 3 of the collar 1, held substantially perpendicular to the plane of the collar by one of its ends.

The stress gauge(s) are instrumented, according to a technique known, with an electric measuring device, capable of measuring the resistance variations of the gauge. Such a device, after calibration, enables to retrieve the deformation of test piece.

Advantageously, the resilient blade is pre-stressed, i.e. stressed even when the collar is at rest, so that the values measured by the electrical measuring device are reliable and continuous.

The stress gauge(s) may be slaved to the resilient blade by gluing.

In an embodiment, the contact finger 8 is arranged substantially perpendicular to the resilient blade 7. The collar exhibits a first means for adjusting the position of the contact finger relative to said resilient blade.

As illustrated on FIGS. 1 and 2, the contact finger 8 is threaded, in particular in the form of a screw, and capable of co-operating with the internal screw thread of a bore provided at one of the free ends 3 of the ring 2. The contact finger 8 is then screwed, mounted as a through-piece at a flank 15 extending upwards from such a protrusion forming such a free end 3.

In an embodiment, one of the free ends 3 of the ring 2 exhibits a clamping jaw 9, capable of maintaining said resilient blade 7.

As illustrated on FIG. 1, such a material protrusion, forming such a free end 3, shows a shoulder against which a cheek 16 clamps the resilient blade 7, at the lower end thereof, in particular by means of a locking screw 17.

A cover (not illustrated) may be provided to protect the resilient blade 7. The cover may be provided removable, in particular slaved to the cheek 16 of the clamping jaw 9. The cover extends upwards over the whole height of the blade 7 and shows an internal volume inside which the blade 7 may be clamped during the deformation of the collar.

In an embodiment, the free ends 3 of the ring 2 are connected by extended resilient means 10. The resilient means 10 enable advantageously to pre-stress the resilient blade 7. The collar may exhibit moreover means for adjusting the recall force of the resilient means 10.

The resilient means 10 may in particular be in the form of an extended spring or in the form of an O-ring.

Both free ends 3 of the ring 2 may be connected by resilient means 10 at two catching points 11, 12, wherein the collar exhibits moreover second means 13, 14 for adjusting the position of a catching point 12 relative to one of the free ends 3 of the ring 2.

Said second setting means are illustrated for instance on FIGS. 1 and 2. For easier illustration, said second setting means have been illustrated below the free ends 3 of the collar on FIG. 1 and in the extension of said free ends 3 on FIG. 2.

Also, advantageously, a catching point 13 is formed by an element mounted slidingly, along the longitudinal direction of the resilient means, at such a free end 3 of the ring. Such element is tapped, to be traversed by a positioning screw 14, capable of bearing upon one side of such a free end 3.

In a non-illustrated embodiment, both free ends 3 of the ring are, in particular, traversed by a guiding rod, in particular at a bore running through said free ends 3.

This guiding rod, mounted slidingly at least as such a free end 3, sees to it that the collar 1 deforms in a controlled fashion, in particular without any twist, so that said free ends 3 are kept substantially opposite to one another.

However, the invention also relates to a sheath 20, intended for being used in a test cell, such as that for instance described in document FR-2,663.121, in order to protect a test piece 21, in particular mineral, rock, soil, or concrete. The sheath 20 is formed of a resilient sleeve 22, being capable in particular of co-operating with a measuring collar according to the invention.

According to the invention, the sleeve 22 exhibits in its wall at least two hard spots 24, spread regularly on the circumference of said sleeve 22 and capable of forming resting points for said collar 1. The sleeve can be realized from an elastic diaphragm in particular from of an elastomer.

Figure 4:
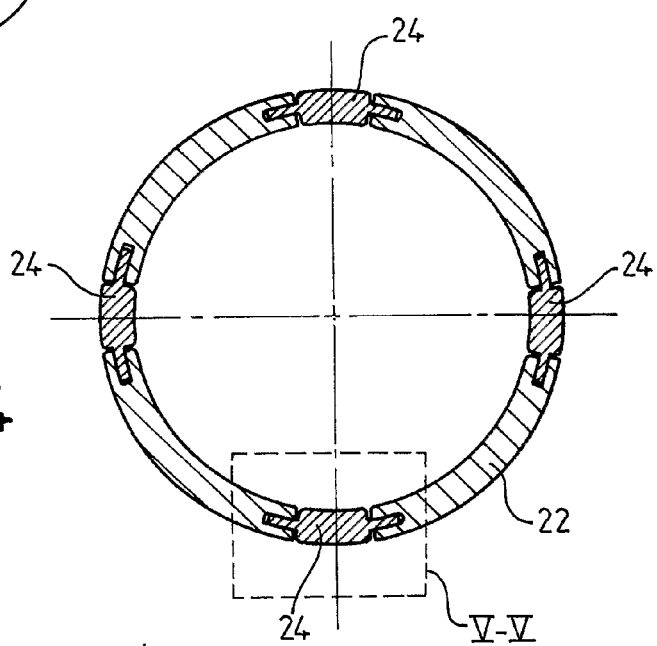
FIG. 4 is a horizontal sectional view IV-IV, as illustrated on FIG. 3.

As illustrated on FIG. 4. The sleeve exhibits, according to an embodiment, four points spread regularly on the circumference of said sleeve at 90°.

Such hard spots will be advantageously formed by a material exhibiting a stiffness greater than the diaphragm and a stiffness greater than the sample so that their deformation is negligible relative to the deformation of the test piece. Such hard spots might be formed in particular of a metal matter.

According to an embodiment, each hard spot 24 is formed of an insert, of thickness substantially equal to the thickness of the wall of the sleeve, and flush with both sides of said wall. The insert exhibits moreover interlocking means 25, 26 for retaining said insert to the sleeve.

The interlocking means might be formed by a lateral lug 25, capable of extending, along the wall of the sleeve, as shown on FIG. 4, inside a mortice 26 arranged in said wall so as to form a baffle providing for the tightness of the sleeve to fluid.

Figure 3:
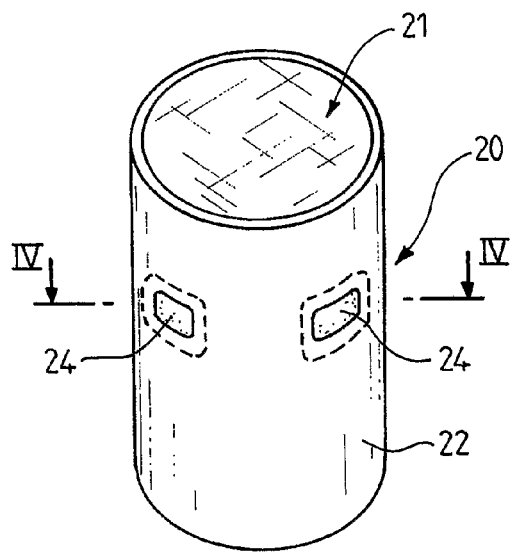
FIG. 3 is a perspective view of a protective sheath according to the invention.

Advantageously, as illustrated as a dotted line on. FIG. 3, the lateral lug is continuous on the periphery of the insert.

Figure 5:
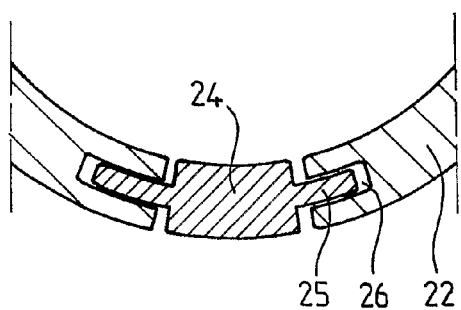
FIG. 5 is a detailed sectional view as illustrated in the frame V-V.

Thus, as illustrated on FIG. 5, during the deformation of the diaphragm, the lug 25 is capable of sliding in the mortice 26 arranged in the diaphragm providing for the tightness function even during deformations.

The insert can be advantageously arc-shaped by a curving radius substantially equal to the curving radius of the wall of the sleeve.

Advantageously, the lateral lug is advantageously arc-shaped similarly.

The sleeve can be in particular made of silicon. The sleeve is advantageously compound-filled in a mold where the inserts are pre-positioned. For instance, the molding operation is performed under vacuum to prevent the occurrence of inclusions, in particular bubbles.

Naturally, other embodiments, understandable to the man of the art, could have been contemplated without departing from the framework of the invention.

I claim:

1. A testing apparatus for measuring lateral deformation of a test piece during triaxial compression tests, the testing apparatus comprising:
    a collar formed of a single ring having free ends spaced by a distance, said single ring being formed of a metal material or a composite material, said collar having a means for measuring the distance between said free ends, said means for measuring comprising:
        a flexible blade fitted with at least one stress gauge, said flexible blade being pre-stressed and fastened to one of said free ends of said single ring;
        a contact finger fastened to the other of said free ends of said ring, said contact finger extending perpendicular to said flexible blade, said contact finger suitable for causing a bending of said flexible blade during a deformation of said collar; and
        a means for adjusting a position of said contract finger in relation to said flexible blade; and
    a sheath encircled by said single ring such that said single ring grips said sheath, said sheath suitable for protecting the test piece, said sheath having a flexible sleeve, said sleeve having at least a pair of hard spots evenly spaced from each other around a circumference of said sleeve so as to form support points for said collar, each of the hard spots being an insert having a thickness substantially equal to a thickness of a wall of said sleeve, said insert having sides flush with both sides of said wall of said sleeve, said insert having therein means for interlocking said insert on said sleeve.

2. The testing apparatus of claim 1, said contact finger being threaded, the other of said free ends having an internally threaded bore formed therein, said contact finger being threadedly received by said bore.

3. The testing apparatus of claim 1, said one of said free ends having a clamping jaw, said clamping jaw receiving said flexible blade therein.

4. The testing apparatus of claim 2, said free ends being interconnected by an elastic member.

5. The testing apparatus of claim 4, said elastic member having means for adjusting a restoring force thereof.

6. The testing apparatus of claim 5, each of said free ends having a catching point, said elastic member received by the catching points, said collar having a means thereon for adjusting a position of at least one of the catching points relative to the free end.

7. The testing apparatus of claim 2, said means for interlocking comprising a lateral lug extending from said insert, said wall of said sleeve having a mortice formed therein, said lateral lug received in said mortice so as to form a baffle so as to provide fluid tightness to said sleeve.

8. The testing apparatus of claim 1, said insert having an arcuate shape having a curving radius substantially equal to a curving radius of said wall of said sleeve.

* * * * *